United States Patent
Agronskaja et al.

(10) Patent No.: US 7,671,333 B2
(45) Date of Patent: Mar. 2, 2010

(54) APPARATUS FOR OBSERVING A SAMPLE WITH A PARTICLE BEAM AND AN OPTICAL MICROSCOPE

(75) Inventors: Alexandra Valerievna Agronskaja, Houten (NL); Hans Casper Gerritsen, Doorn (NL); Adrianus Johannes Verkleij, Nieuwegein (NL); Abraham Johannes Koster, Amsterdam (NL)

(73) Assignee: FEI Company, Hillsboro, OR (US)

( * ) Notice: Subject to any disclaimer, the term of this patent is extended or adjusted under 35 U.S.C. 154(b) by 121 days.

(21) Appl. No.: 12/026,419

(22) Filed: Feb. 5, 2008

(65) Prior Publication Data
US 2008/0210869 A1    Sep. 4, 2008

(30) Foreign Application Priority Data
Feb. 5, 2007    (EP)    .................. 07101725

(51) Int. Cl.
G01N 13/12    (2006.01)
H01J 37/20    (2006.01)
H01J 37/28    (2006.01)
H01J 37/244    (2006.01)

(52) U.S. Cl. ................ 250/311; 250/310; 250/398; 250/397; 250/396 R; 250/440.11

(58) Field of Classification Search ................ 250/311, 250/310, 398, 397, 396 R, 440.11
See application file for complete search history.

(56) References Cited

U.S. PATENT DOCUMENTS

| | | |
|---|---|---|
| 3,740,147 A | 6/1973 | Kallet |
| 4,379,230 A | 4/1983 | Bouwhuis et al. |
| 4,440,475 A | 4/1984 | Colliaux |
| 5,168,166 A | 12/1992 | Hayakawa et al. |
| 5,808,790 A | 9/1998 | Otaki |

(Continued)

FOREIGN PATENT DOCUMENTS

FR    2596863    9/1987

(Continued)

OTHER PUBLICATIONS

Reimer, Ludwig, "Transmission Electron Microscopy: Physics of Image Formation and Microanalysis," 1984, pp. 110-111.

Primary Examiner—Nikita Wells
(74) Attorney, Agent, or Firm—Scheinberg & Griner, LLP; Michael O. Scheinberg; David Griner

(57) ABSTRACT

An apparatus for observing a sample (1) with a TEM column and an optical high resolution scanning microscope (10). The sample position when observing the sample with the TEM column differs from the sample position when observing the sample with the optical microscope in that in the latter case the sample is tilted towards the light-optical microscope. By using an optical microscope of the scanning type, and preferably using monochromatic light, the lens elements (11) of the optical microscope facing the sample position can be sufficiently small to be positioned between the pole faces (8A, 8B) of the (magnetic) particle-optical objective lens (7). This is in contrast with the objective lens systems conventionally used in optical microscopes, which show a large diameter. Furthermore the optical microscope, or at least the parts (11) close to the sample, may be retractable so as to free space when imaging in TEM mode.

15 Claims, 3 Drawing Sheets

U.S. PATENT DOCUMENTS

| | | | |
|---|---|---|---|
| 5,811,804 A * | 9/1998 | Van Blitterswijk et al. .. 250/311 |
| 5,905,266 A | 5/1999 | Larduinat et al. |
| 6,373,070 B1 | 4/2002 | Rasmussen |
| 7,139,071 B2 | 11/2006 | Bennett et al. |
| 7,154,091 B2 | 12/2006 | Zewail et al. |
| 7,420,184 B2 | 9/2008 | van de Water et al. |
| 2002/0166976 A1 * | 11/2002 | Sugaya et al. .......... 250/440.11 |
| 2007/0115468 A1 * | 5/2007 | Barnard ................. 356/300 |

FOREIGN PATENT DOCUMENTS

| | | |
|---|---|---|
| WO | WO9958939 | 11/1999 |
| WO | WO02/075292 | 9/2002 |
| WO | WO2005/098895 | 10/2005 |

* cited by examiner

APPARATUS FOR OBSERVING A SAMPLE WITH A PARTICLE BEAM AND AN OPTICAL MICROSCOPE

BACKGROUND OF THE INVENTION

The invention relates to a particle-optical apparatus for imaging a thin sample using a beam of particles and for imaging the sample with light, the apparatus comprising
- a particle source for producing a beam of particles along a particle-optical axis,
- particle-optical lenses arranged round the particle-optical axis for manipulating said beam of particles,
- a sample manipulator for positioning the sample on the particle-optical axis and between the pole faces of one of the particle-optical lenses, the so-named particle-optical objective lens, said sample manipulator capable of tilting the sample with respect to the particle-optical axis,
- a detector for detecting particles transmitted through the sample, and
- a light-optical microscope.

Such an apparatus was sold by Akashi Seisakusho Ltd, Japan, under the name LEM-2000.

The known apparatus comprises a Transmission Electron Microscope column (TEM column) and an optical microscope. It is equipped to observe samples mounted on large 7 mm grids with the light microscope or in the TEM column.

The optical microscope is mounted at the front side of the apparatus—that is: the side where the operator resides—. The optical microscope has a binocular and the operator observes a sample that is mounted vertically (the optical path is bent by a prism over 90 degrees). The magnification of the optical microscope is between 50× and 250×. A condenser illuminates the sample through the grid. The sample resides in atmosphere when observed with the optical microscope.

Behind the optical microscope a TEM column is mounted in horizontal position. The TEM operates with an electron energy of up to 100 keV and uses 6 electron optical lenses. Transmitted electrons are imaged on a fluorescent screen with a magnification of between 250× and 45000×. The fluorescent screen can be observed with binoculars, or the screen can be temporarily exchanged for a film cassette to make photos.

The TEM column comprises a sample chamber in which the sample must be placed for observation. The sample chamber is evacuated when observing the sample in the TEM.

A shuttle mechanism transports the sample from a first position where it is observed with the optical microscope to a second position where it is observed in the TEM. To that end the sample is transferred through an airlock.

A disadvantage of the known apparatus is that the sample must be transferred between two observation positions: one for the optical microscope located in air and another for the TEM located in a vacuum environment. Therefore the sample must pass through an airlock when travelling between the two observation positions. This results in relative large positional inaccuracies when the sample is placed in the TEM, resulting in long delays to determine the exact position. Especially for modern types of TEM's with resolutions down to 0.1 nm or better, the mapping of the optical microscope image to the TEM image will be very time consuming. When a sample has to be observed repeatedly with the optical microscope and the TEM, the sample must be positioned accurately in the TEM column repeatedly, resulting in long delay times.

Another disadvantage is that the sample must pass through an airlock between the optical microscope and the TEM. As a result of this a delay due to pump down or due to venting occurs when the sample is travelling through the airlock.

When a sample has to be observed repeatedly with the optical microscope and the TEM, the sample must pass through the airlock repeatedly, and must be positioned accurately in the TEM column, resulting in long delay times.

A further disadvantage is that the sample is in atmosphere when observed with the optical microscope, and in vacuum when observed in the TEM. This can result in warping of the sample, as well as in changes in the sample due to boiling, outgassing, etc. Comparison and/or mapping of images obtained by the two techniques (particle-optical inspection and inspection with an optical microscope) may be hampered by this. Also, when the sample is passed through the airlock repeatedly because it must be observed by the optical microscope and the TEM repeatedly, the repeated evacuating the sample and exposing it to air again can cause the sample to change after each evacuation/venting cycle. This may result in poor comparison/mapping of the sample even in subsequent vented and/or evacuated situation.

The invention aims to provide an apparatus overcoming said disadvantages.

BRIEF SUMMARY OF THE INVENTION

The invention relates to an apparatus for observing a sample with a TEM column and an optical high resolution scanning microscope. In one embodiment, the sample position when observing the sample with the TEM column differs from the sample position when observing the sample with the optical microscope in that in the latter case the sample is tilted towards the light-optical microscope. By using an optical microscope of the scanning type, and preferably using monochromatic light, the lens elements of the optical microscope facing the sample position can be sufficiently small to be positioned between the pole faces of the (magnetic) particle-optical objective lens. This is in contrast with the objective lens systems conventionally used in optical microscopes, which show a large diameter. Furthermore the optical microscope, or at least the parts close to the sample, may be retractable so as to free space when imaging in TEM mode.

BRIEF DESCRIPTION OF THE DRAWINGS

The invention is now further elucidated on the basis of schematic drawings, in which corresponding features are identified by identical numerals. To this end.

DETAILED DESCRIPTION OF PREFERRED EMBODIMENTS

Figure 1:
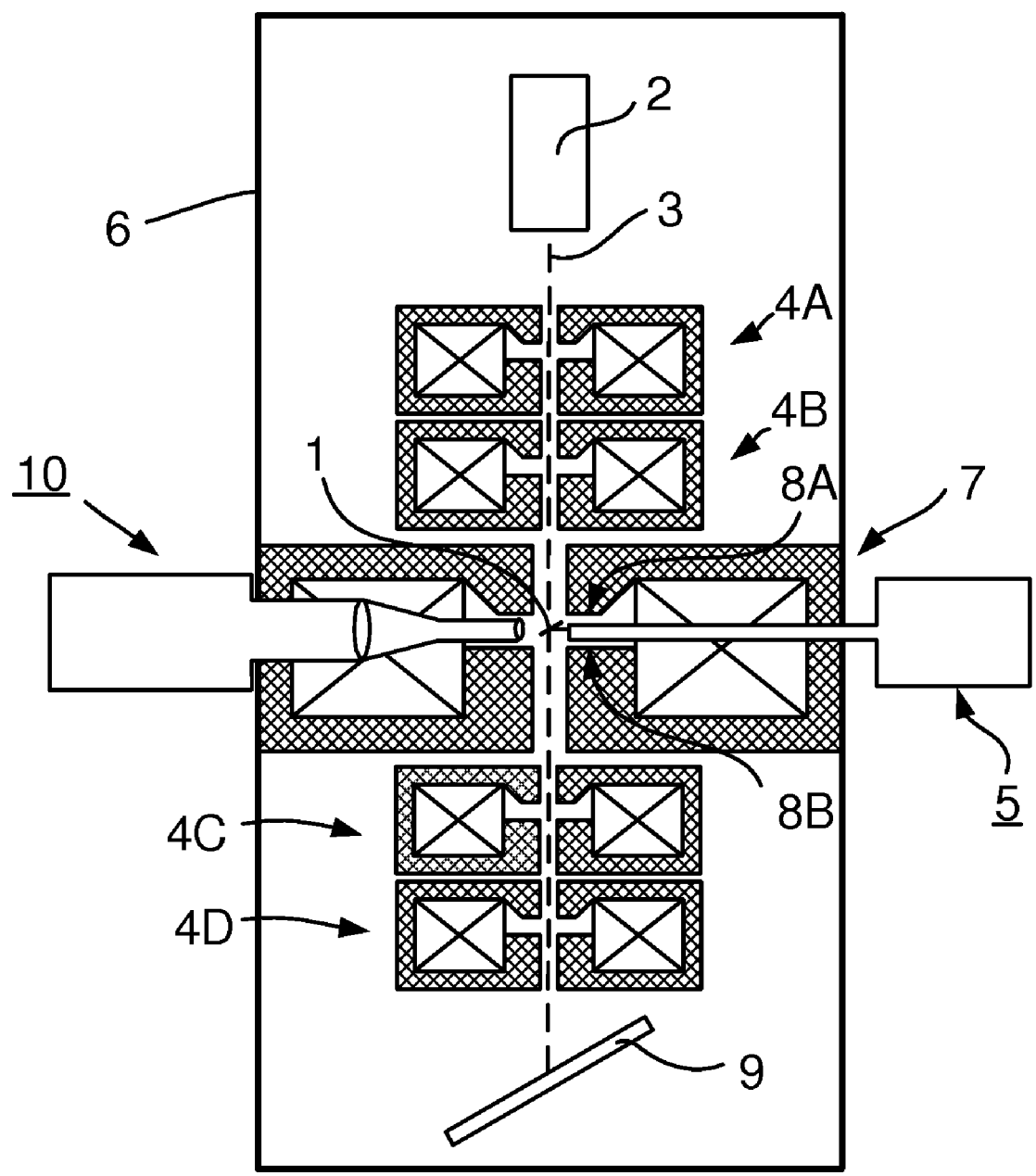
FIG. 1 shows an apparatus according to the invention.

To that end the apparatus according to the invention is characterized in that
- the light-optical microscope is equipped to image the sample while the sample is positioned substantially on the particle-optical axis and tilted such, that the sample faces the light-optical microscope,
- the light-optical microscope is a so-named scanning light-optical microscope, equipped to illuminate the sample with a point of light, the point of light formed by a focussing unit, the light-optical microscope equipped to scan the point of light over the sample, and at least the focussing unit is retractably mounted so as to free space between the pole pieces when the sample is imaged using the beam of particles.

By using a light-optical microscope equipped to image the sample while on the particle-optical axis, and using the sample manipulator for re-positioning the sample such that it faces the light-optical microscope, a much improved coincidence between particle-optical image and light-optical image can be obtained. As known to the person skilled in the art of sample manipulators for particle-optical apparatus, such as commonly used in a TEM, such sample manipulators often show a positional reproducibility and accuracy of better than 200 nm translational and 0.1 degrees rotational/tilt, with step sizes even smaller. The resultant high positional accuracy enables easy mapping of the optical microscope's image to the TEM image.

The sample position where the light-optical microscope and particle-optical beam image the sample is in the same (vacuum) environment as the first sample position. Therefore the sample need only be evacuated once, even when repeatedly observed with the optical microscope and the TEM. Therefore delay resulting from repeated pumping and venting is eliminated.

As the sample is kept in the same vacuum environment during observation, no deformation and/or warping will occur due to repeated exposure to vacuum or air.

By equipping the optical microscope such that the sample is scanned with a point of light, the resolution obtained with the light microscope is not limited by the aberrations occurring in the detection path, but only in the illumination path, in which the diameter of the point of light generated. Such a method in which the sample is scanned with a point of light is known from e.g. scanning optical microscopy, where the sample is illuminated with a small focus that is scanned over the surface of the sample. This enables the use of high-resolution optical lens systems with a much smaller diameter than the diameter of conventional optical objective lens systems. The reason for this is as follows:

High-resolution optical objective lens systems have high numerical apertures and short working distances of e.g. 1 mm or less. Therefore the optical objective lens system needs to be placed close to the sample position, and the diameter of the optical element facing the sample needs to be large (due to the required high numerical aperture normally a lens diameter equal to or larger than the working distance). Conventional optical microscope objectives need to be corrected for lens aberrations, demanding a multitude of lenses close to the sample position, and many of these lenses typically have a diameter larger than the lens closest to the sample. As a result a conventional optical microscope objective is a complex unit, having a diameter many times larger than the distance between the lens closest to the sample and the sample itself. Therefore high-resolution objectives have a diameter too large to fit between the pole faces. Also their construction, in which optical elements are kitted together, is often incompatible with the vacuum of the sample position, typically $10^{-6}$ mbar or less.

Contrary to this the objective used in e.g. scanning optical microscopy need not be compensated for aberrations in the detecting path when viewing thin samples, as these do not affect the image quality. This is due to the fact that, at a certain moment in time, all light emanating from the sample emanates from one point only: the point where the beam impinges on the sample. The spatial resolution is thus a direct result of the diameter of the point that is formed on the sample, and is not influenced by lens aberrations in the detection path. As a result the optical objective lens can be of a relatively simple construction, e.g. an aspherical singlet. Such a singlet can have a much reduced outer diameter when compared to a conventional optical microscope objective with similar resolution and working distance.

The point of light can be scanned over the sample by e.g. one or two movable mirrors in the illuminating optical path. By tilting the one or more mirrors with e.g. piezo-actuators or using electric coils and a magnet, the beam is deflected, resulting in a different position where the beam impinges on the sample.

An additional advantage of scanning the beam of light over the sample is that the magnification of the image is simply changed by changing the scan amplitude. Changing the scan amplitude is done by changing the amplitude of the actuators moving the mirror(s), e.g. by changing an electric signal. This eliminates the need to change the objective lens system, which is normally done when using conventional optical objective lens systems. It is remarked that, as the objective lens system is placed in a vacuum environment and the space around the objective lens system is limited, changing of the objective lens system would be more difficult than in a conventional optical microscope.

It is noted that the use of a focused beam of light that is scanned over the sample is of special interest for observation methods in which high photon densities are required, such as observation methods using multi-photon excitation or ($2^{nd}$) harmonic frequency generation in the sample. Irradiating a large area of the sample with such high levels of electromagnetic radiation would result in high temperatures in the sample and possibly ablation of the sample. It also puts unnecessary high demands on the intensity of the light source used.

It is further noted that the focussing system focusing the light on the sample—in most cases a lens—must form a fine focus on the sample. Lens aberrations that do not influence the diameter of the focus, such as field curvature, can be ignored, or e.g. corrected for in the scan system of the light-optical microscope. If the illuminating beam is sufficiently monochromatic, chromatic aberrations of the lens do not influence the diameter of the focus either, and thus do not deteriorate the resolution, even when the light that is detected is of a different colour than the light illuminating the sample. The latter occurs when detecting e.g. luminescence (fluorescence and/or phosphorescence) of the sample, and in e.g. Fluorescent Resonant Energy Transfer (FRET) and Fluorescent Lifetime IMaging (FLIM) techniques.

By using a retractable light-optical microscope the space around the sample position is freed when imaging the sample with the particle beam. This enables e.g. larger movements of the sample, and is thereby beneficial for e.g. the insertion of a detector.

It is noted that to free the space around the sample position it suffices when the elements of the light-optical microscope closest to the sample position can be retracted. Other parts of the light-optical microscope may be left in place.

It is further noted that e.g. X-ray detectors for use with a TEM are often retractably mounted. By retracting the light-optical microscope and inserting the X-ray detector and vice versa, the space around the sample position is used effectively. Also the air-lock mechanism used to introduce samples to the sample position and to couple the sample to the sample manipulator, as used in some TEM's, may interfere with the light-optical microscope when it would not be retracted.

In an embodiment of the apparatus according to the invention the focussing unit also gathers light emanating from the sample for imaging the sample.

In this embodiment the lens of the light-optical microscope facing the sample is used for both irradiating the sample with a focused beam of light and for detecting light coming from the sample.

In another embodiment of the apparatus according to the invention the light detected from the sample to form the image does not pass through the focussing unit.

In this embodiment the detected light follows a different path. It may e.g. be gathered by a lens positioned at the side opposite to the side facing the focussing unit, but it may e.g. also be detected by a detector such as a photomultiplier tube positioned at that opposite side.

In a further embodiment of the apparatus according to the invention the light detected from the sample emanates from the side of the sample opposite to the side of the sample that is illuminated.

In another embodiment the point of light is formed from monochrome light.

In this embodiment the illuminating optical path uses only one colour, and thus chromatic aberrations are of no consequence in the illuminating path either. Therefore no correction for chromatic aberration is needed in either the illuminating optics or the imaging optics (used in the detection path), resulting in simpler lens elements.

It is remarked that optical lens systems are known that are corrected for e.g. two colures of light. In that case the light may consist of two colours.

In a further embodiment of the apparatus according to the invention the light-optical axis is substantially perpendicular to the particle-optical axis.

The space between the pole pieces of the objective lens is rather limited. The easiest access to the sample position (between the pole faces and near the particle-optical axis) is by using a light-optical microscope with a light-optical axis perpendicular to the particle-optical axis, and inserting/retracting the optical microscope perpendicular to the particle-optical axis.

In yet another embodiment of the apparatus according to the invention the sample position is at least partially surrounded by cryo-shields, thereby enabling imaging of cryogenic samples.

Particle-optical apparatus where a cryogenically cooled sample may be imaged, such as a cryo-TEM, are known per se. An example is the Tecnai G2 Polara, commercially available from FEI Company, Hillsboro (Oreg.), USA. In such instruments the sample manipulator and the vicinity of the sample position are cooled to cryogenic temperatures, e.g. the temperature of boiling nitrogen or boiling helium. By cooling the vicinity of the sample position likewise, a cryogenically cooled sample can be observed with both the particle beam and the optical microscope.

In a further embodiment of the apparatus according to the invention at least the parts of the light-optical microscope facing the sample are equipped to be cooled to a cryogenic temperature, thereby avoiding warming of a cryogenic sample during observation by the light-optical microscope.

By cooling e.g. the lens of the light-optical microscope facing the sample warming of the sample is avoided. Cooling the lens can be done by actively cooling the lens itself (that is: by offering a path with low thermal resistance between the lens and a cold source), or by thermally isolating the lens, thereby allowing the lens to come to a thermal equilibrium with e.g. cryo-shields and/or the sample.

In another embodiment according to the invention the light-optical microscope is further equipped to form an image illuminating the sample with a non-focused beam.

By using a light-optical microscope that is also capable to work as a conventional microscope, a quick image of the sample can be made, possibly at reduced resolution, and a more detailed image can be recorded in scanning mode of the light-optical microscope.

It is noted that, when illuminating the sample with a non-focused beam of light, the detected light can either be reflected light and transmitted light.

It is further noted that the quality of this image need not be of the quality normally expected from an optical microscope objective, as it is used for 'navigation' of the high-resolution image only.

FIG. 1 shows a vacuum chamber 6 in which a particle source 2 is located. The particle source generates a beam of particles, e.g. in the form of an electron beam in which the electrons have an energy of e.g. 300 keV, along particle-optical axis 3. The electron beam is manipulated (focused) by particle-optical lenses 4A, 4B arranged round the particle-optical axis.

Sample manipulator 5 is used to position a sample 1 onto the first sample position, where the beam of particles impinges on the sample. The first sample position is located between the pole faces 8A, 8B of the particle-optical objective lens 7.

The part of the electron beam transmitted through the sample is imaged by the particle-optical lenses 4C, 4D on a detector 9 in the form of e.g. a fluorescent screen or a CCD camera (or a camera of another principle). Also photographic film may be used to detect the particles. Other detectors, such as Electron Energy Loss Spectroscopes (EELS), may be used.

A light-optical microscope 10 enables observation of the sample when it is in the sample position, but tilted to the light-optical microscope.

As mentioned earlier the sample is normally a flat, very thin sample. For high resolution images the sample is often less than 100 nm thick, preferably even less than 50 nm thick. Such a sample is very fragile and therefore it is supported on a grid, e.g. a copper grid, said grid mounted on the sample manipulator 5. Such grids are known to the person skilled in the art as TEM grids.

To observe an area of interest of the sample with the particle beam the area of interest is brought on the particle-optical axis with the sample manipulator 5. While observing the sample with the particle beam, the orientation of the sample can be perpendicular to the particle-optical axis, but for certain techniques, such as 3D tomography, the sample may also be tilted with respect to the particle-optical axis.

To enable positioning the sample to meet these demands, the sample manipulator is able to position the sample with e.g. 3 translational and 2 rotational degrees of freedom, although also sample manipulators with less or even more degrees of freedom are known.

All sample positions/orientations that may be used to image the sample with the particle beam are referred to as the first sample position.

The optical microscope 10 observes a position between the pole faces 8A, 8B. To form the best image with the optical microscope the sample needs to be tilted to a position substantially perpendicular to the optical axis of the optical microscope.

The optical microscope, or at least that part of the optical microscope closest to the particle-optical axis, is retractably mounted, and can be retracted to offer more space round the sample when the sample is not observed with the optical microscope. This additional space may be needed to offer access to the sample by e.g. other types of detectors, such as the commonly known secondary electron detectors, X-ray detectors, etc. that may be used to gather information about the sample when the sample is irradiated with the electron beam.

It is remarked that in this figure sample manipulator 5 and optical microscope 10 are depicted as sharing a plane perpendicular to the particle-optical axis 3 and are positioned opposite to each other. This is not necessary, and also embodiments where the manipulator and optical microscope are in a plane but spaced e.g. 90 degrees or 120 degrees apart, are possible. It is also possible that one or both elements show a symmetry axis that is not perpendicular to the particle-optical axis.

Figure 2:
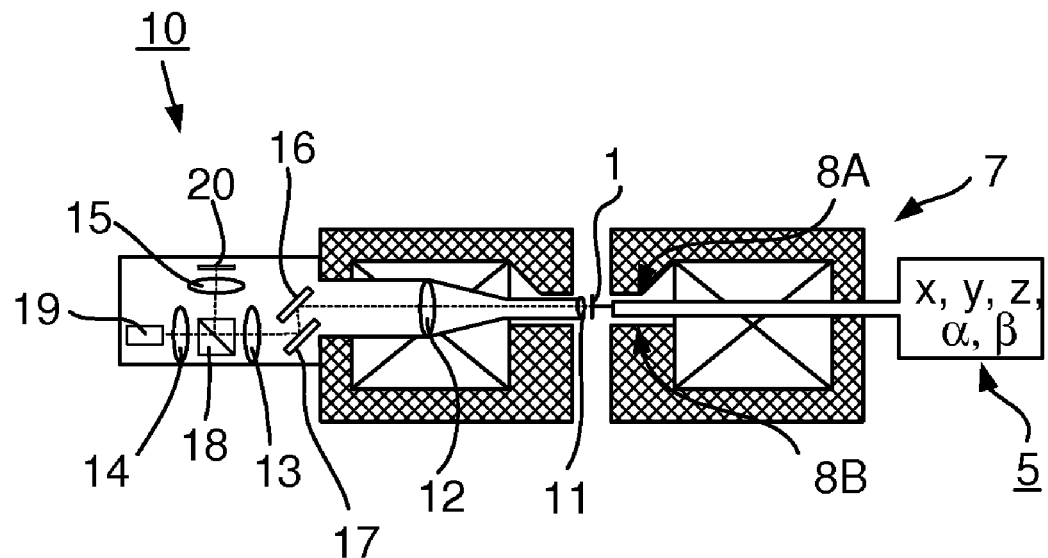
FIG. 2 shows a detail of the apparatus according to the invention.

FIG. 2 shows a detail of the apparatus according to the invention.

FIG. 2 shows the particle-optical objective lens 7, showing the two pole faces 8A, 8B. The sample manipulator 5, here shown capable of positioning the sample 1 with 5 degrees of freedom, is connected with the sample 1. The sample faces the optical microscope 10.

The optical microscope comprises a laser unit 19, producing a beam of light. This beam of light is parallelized with lens 14, then passes through a beam splitter 18, and then impinges on mirrors 17 and 16. These mirrors are mounted on actuators, e.g. piezo actuators, and can thereby change the direction of the beam. The beam is then imaged with two lenses 12, 11 onto the sample (although more lenses may be used).

Lens 12 images the rotational plane of the mirrors 16, 17 in the vicinity of lens 11. In other words: the beam is imaged in such a way that tilting of the beam in lens 11 occurs with a minimal displacement of the beam in that lens. As a result the field of view of the optical microscope is large compared to an optical microscope without such a lens.

Light emanating from the sample, such as reflected light or fluorescent light, is gathered by lens 11, and follows the way back until it comes to the beam splitter 18. The detected light is then deflected to a photonic detector 20. A lens 15 may help focussing the light on the detector. The detector may be a single photon detector, or a more conventional detector, depending on the sensitivity needed.

As the laser 19 produces a monochromatic beam of light, the aberration coefficients of all optical elements can be optimized for the wave length of that light. The chromatic error of the lenses do not affect the image quality. Monochromatic light must in this context be interpreted as light showing sufficient small spread in wavelength so as to avoid the formation of a focus with a diameter that is dominated by chromatic aberration(s). The light coming from the sample travelling to the detector may be of a different colour (e.g. because fluorescent light is detected), but as mentioned earlier lens aberrations occurring in the imaging path do not affect the image quality/resolution.

It is remarked that also illumination optics may be constructed that are compensated for chromatic aberrations on two or more wavelengths and still show diameters of those lens elements that are placed between the pole faces that are sufficiently small.

It is to be mentioned that coatings, reflection of the beam splitter and such may need to be optimized for the wave length of the detected light as well.

It is further mentioned that the optical microscope shown here is drawn very schematic, and that many differences may occur. It is e.g. possible to insert an optical fibre between lens 14 and mirror 19, a so-named laser fiber coupling, thereby enabling the laser and detector to be placed away from the column of the apparatus. An optical fiber may also be placed between lens 15 and detector 20, a so-named detector fiber coupling. The beam splitter may also be a grating, and lenses may be added or eliminated according to the exact implementation of the optical microscope. Also e.g. a beam polarizer may be incorporated into the optical microscope.

It is also remarked that, as no absolute monochromaticity of the illuminating beam is required, but only such monochromaticity so as to form a focus that is not dominated by chromatic aberration, also light filtered with a colour filter from e.g. a device emitting white light can be used.

Figure 3:
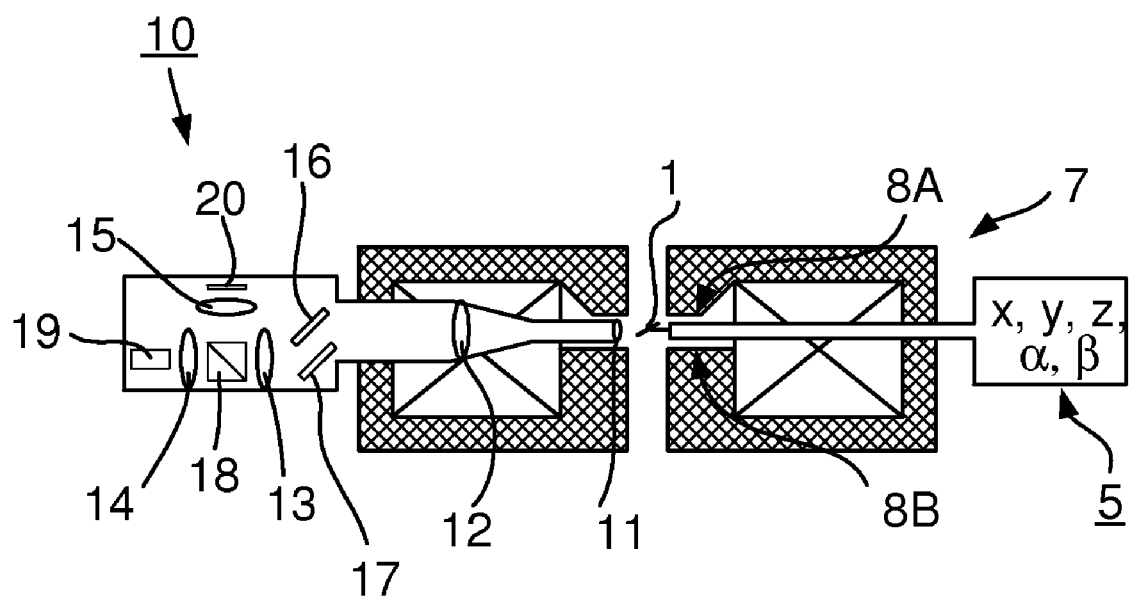
FIG. 3 shows a detail of the apparatus according to the invention, where the optical microscope is retracted.

FIG. 3 shows a detail of the apparatus according to the invention, where the optical microscope is retracted.

FIG. 3 can be thought to be derived from FIG. 2. As can be seen, the optical microscope 10 is slightly retracted, thereby freeing the space around the first sample position. Hereby the sample 1 can be positioned freely between the pole faces (pieces) 8A, 8B without contacting the optical microscope. The retraction may also enable other parts of the apparatus, such as e.g. X-ray detectors, secondary electron detectors, etc., to be positioned near the sample.

It is remarked that in this figure it is shown that the whole optical microscope 10 is retracted. It will be recognized by the person skilled in the art that it is sufficient when only part of the optical microscope, the part comprising the lens 11 and its mounting, is retracted.

Figure 4:
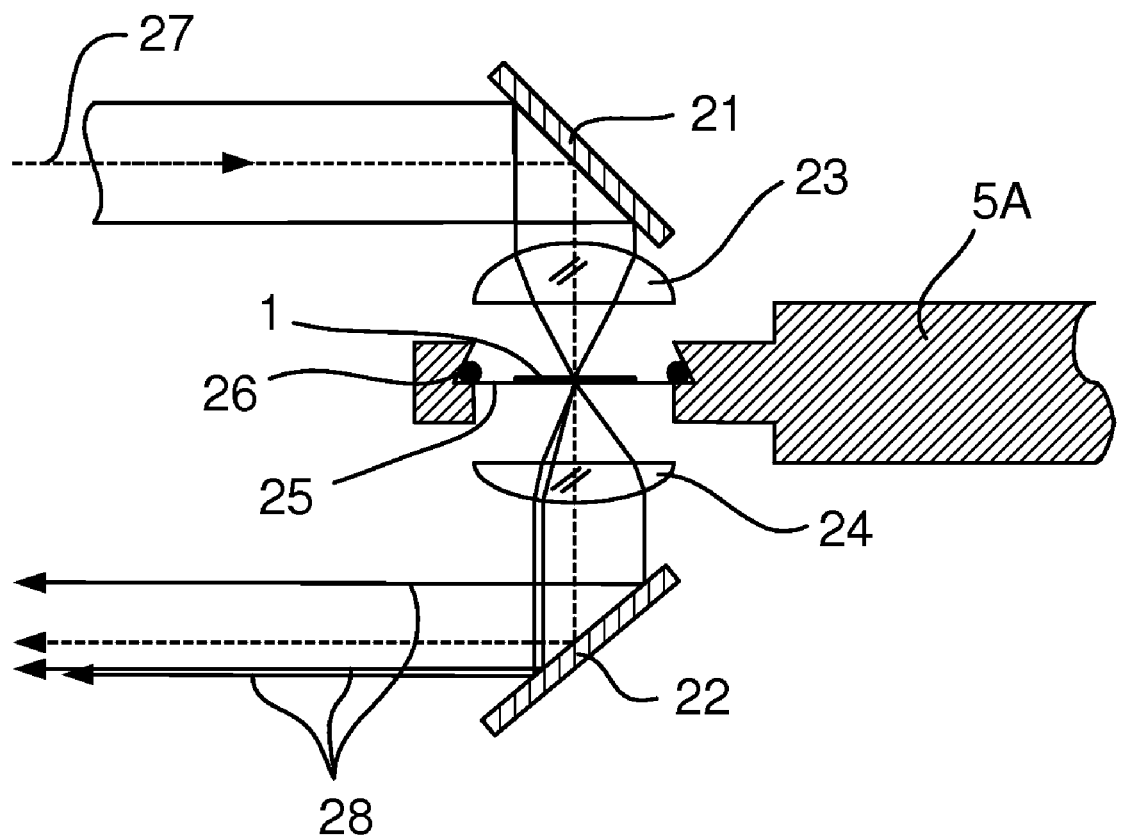
FIG. 4 shows a detail of the apparatus according to the invention, where the sample is illuminated at one side and observed at the other side.

FIG. 4 shows a detail of the apparatus according to the invention, where the sample is illuminated at one side and observed at the other side.

FIG. 4 shows an incoming beam of light round optical axis 27, which is deflected by mirror 21 towards the sample 1. A lens 23 focuses the light onto the sample. The sample is mounted on a TEM grid 25, which is held in place on the distal end 5A of the sample manipulator with a circular spring 26. Light emitted by the sample or transmitted through the sample, depicted by rays 28, is gathered by lens 24 and deflected by mirror 22 in a direction parallel to the incoming beam of light. The particle-optical axis is e.g. perpendicular to the plane of the figure.

It is remarked that the beam of light may be scanned over the sample with other mirrors, but that it can also be envisaged that mirror 21 is used for the scanning. In that case the mirror 21 must by actuated by actuators. It is also envisaged that the sample itself is moved with respect to the microscope by a scanning movement of the (distal end of the) sample holder 5A

It is also noted that, instead of guiding the light to and from the sample with mirrors (21, 22), e.g. optical fibres may be used.

It is further noted that the two lenses 23, 24 can be inserted/retracted in such a way that the beam 27 between the lenses is parallel to the particle-optical axis. In that case the sample need not be repositioned/tilted. However, it may be attractive to have the path between the lenses perpendicular to the particle optical axis, as this may enable larger diameters of the lenses and thus a more favourable numerical aperture of the light-optical microscope.

Also noted is that, when detecting reflected light, lens 24 and mirror 22 can be eliminated, and both illuminating light and detected light are guided via lens 23 and mirror 21.

It is even possible to collect the emitted light from both sides of the sample, thereby detecting photons as efficiently as possible.

In the case of e.g. fluorescent microscopy colour filters may be inserted in the path of the detected light to filter out the illuminating light.

It is remarked that each of the embodiments described before can be realized with cooling surfaces and cooling conduits so that the sample can be kept at a cryogenic temperature. Such measures are well known from conventional cryo-TEM's.

We claim as follows:

1. A particle-optical apparatus for imaging a thin sample using a beam of particles and for imaging the sample with light, the apparatus comprising
    a particle source for producing a beam of particles along a particle-optical axis,
    a plurality of particle-optical lenses arranged round the particle-optical axis for manipulating said beam of particles, each particle-optical lens having at least two pole faces,
    a sample manipulator for positioning the sample on the particle-optical axis and between the pole faces of one of the particle-optical lenses, said sample manipulator capable of tilting the sample with respect to the particle-optical axis,
    a detector for detecting particles transmitted through the sample, and
    a light-optical microscope,
characterized in that
    the light-optical microscope is equipped to image the sample while the sample is positioned substantially on the particle-optical axis and tilted such that the sample faces the light-optical microscope,
    the light-optical microscope is a scanning light-optical microscope, equipped to illuminate the sample with a point of light, the point of light formed by a focussing unit, the light-optical microscope equipped to scan the point over the sample, and
    at least the focussing unit is retractably mounted so as to free space between the pole pieces when the sample is imaged using the beam of particles.

2. The apparatus according to claim 1 in which the focussing unit also gathers light emanating from the sample for imaging the sample.

3. The apparatus according to claim 2 in which light emanating from the sample is used to form an image of the sample but said light emanating from the sample does not pass through the focussing unit to form the image.

4. The apparatus according to claim 3 in which the light used to form the image of the sample emanates from the side of the sample opposite the side of the sample that is illuminated.

5. The apparatus according to claim 1 in which the light is monochromatic light.

6. The apparatus according to claim 1 in which the light-optical microscope has a light-optical axis which is substantially perpendicular to the particle-optical axis.

7. The apparatus according to claim 1 in which the positioned sample is at least partially surrounded by cryo-shields, thereby enabling imaging of cryogenically cooled samples.

8. The apparatus according to claim 7 in which at least the parts of the light-optical microscope facing the sample are equipped to be cooled to a cryogenic temperature, thereby avoiding warming of a cryogenic sample during sample illumination by the light-optical microscope.

9. The apparatus according to claim 1 in which the light-optical microscope is further equipped to form an image by illuminating the sample with a non-focused beam of light.

10. A particle-optical apparatus for imaging a sample using a beam of particles and for imaging the sample with light, the apparatus comprising:
    a particle source for imaging the sample, said particle source producing a beam of particles along a particle-optical axis;
    a plurality of particle-optical lenses arranged around the particle-optical axis for manipulating said beam of particles, each particle-optical lens having at least two pole faces,
    a light-optical microscope for imaging the sample while the sample is positioned between the pole faces of one or the particle-optical lenses and substantially on the particle-optical axis, said microscope having a light source and a focussing unit for focussing light from the light source to a point on the sample surface along a light-optical axis, and said point of light being scanned over the sample surface in order to image the sample, and
    said focussing unit being retractably mounted so that it can be extended to image the sample with the light-optical microscope but retracted so as to free space between the pole faces when the sample is imaged using the beam of particles.

11. The apparatus of claim 10 in which the light-optical axis and the particle-optical axis are parallel with the focusing unit extended 12. The apparatus of claim 10 in which the light-optical axis and the particle-optical axis are not parallel with the focusing unit extended and further comprising a sample manipulator for positioning the sample between the pole faces of one of the particle-optical lenses and on both the particle-optical axis and the light-optical axis, said sample manipulator tilting the sample so that a surface of the sample is perpendicular to the particle-optical axis for particle beam imaging and tilting the sample so that said surface is perpendicular to the light-optical axis for imaging with the light-optical microscope.

13. The apparatus of claim 10 in which the light source comprises a laser which produces a. monochromatic beam of light.

14. The apparatus of claim 10 further comprising a retractably mounted X-ray detector that can be extended into the space freed when the focusing unit is refracted.

15. The apparatus of claim 10 in which said focussing unit is refracted or extended by refracting or extending the light-optical microscope.

* * * * *